(12) United States Patent
Drews et al.

(10) Patent No.: US 7,556,647 B2
(45) Date of Patent: Jul. 7, 2009

(54) ATTACHMENT DEVICE AND METHODS OF USING THE SAME

(75) Inventors: Michael J. Drews, Sacramento, CA (US); Donnell W. Gurskis, Belmont, CA (US); Steven R. Bacich, Half Moon Bay, CA (US)

(73) Assignee: Arbor Surgical Technologies, Inc., Irvine, CA (US)

( * ) Notice: Subject to any disclaimer, the term of this patent is extended or adjusted under 35 U.S.C. 154(b) by 973 days.

(21) Appl. No.: 10/681,700

(22) Filed: Oct. 8, 2003

(65) Prior Publication Data

US 2005/0080454 A1    Apr. 14, 2005

(51) Int. Cl.
*A61F 2/24* (2006.01)
*A61B 17/10* (2006.01)
*A61B 17/08* (2006.01)

(52) U.S. Cl. ............ 623/2.11; 606/142; 606/216; 623/904

(58) Field of Classification Search ............ 606/151, 606/219, 215, 221, 139, 148, 216, 142; 623/904, 623/2.11
See application file for complete search history.

(56) References Cited

U.S. PATENT DOCUMENTS

| | | | |
|---|---|---|---|
| 3,143,742 A | 8/1964 | Cromie | |
| 3,371,352 A | 3/1968 | Siposs et al. | |
| 3,464,065 A | 9/1969 | Cromie | |
| 4,345,601 A | 8/1982 | Fukuda | |
| 4,485,816 A * | 12/1984 | Krumme | 606/219 |
| 4,548,202 A | 10/1985 | Duncan | |
| 4,595,007 A | 6/1986 | Mericle | |
| 4,665,906 A | 5/1987 | Jervis | |
| 4,705,516 A * | 11/1987 | Barone et al. | 623/2.39 |

(Continued)

FOREIGN PATENT DOCUMENTS

DE    19711288 A1    10/1998

(Continued)

OTHER PUBLICATIONS

PCT International Search Report for PCT/US2005/043503, Applicant: Arbor Surgical Technologies, Inc., Forms PCT/ISA/210 and PCT/ISA/220, 8 pages.

(Continued)

*Primary Examiner*—(Jackie) Tan-Uyen T. Ho
*Assistant Examiner*—Melissa Ryckman
(74) *Attorney, Agent, or Firm*—William A. English; Vista IP Law Group LLP

(57) ABSTRACT

Devices for attaching a first mass and a second mass and methods of making and using the same are disclosed. The devices can be made from an resilient, elastic or deformable materials. The devices can be used to attach a heart valve ring to a biological annulus. The devices can also be used for wound closure or a variety of other procedures such as anchoring a prosthesis to surrounding tissue or another prosthesis, tissue repair, such as in the closure of congenital defects such as septal heart defects, tissue or vessel anastomosis, fixation of tissue with or without a reinforcing mesh for hernia repair, orthopedic anchoring such as in bone fusing or tendon or muscle repair, ophthalmic indications, laparoscopic or endoscopic tissue repair or placement of prostheses, or use by robotic devices for procedures such as those above performed remotely.

21 Claims, 13 Drawing Sheets

U.S. PATENT DOCUMENTS

| | | | |
|---|---|---|---|
| 4,932,955 | A | 6/1990 | Merz et al. |
| 5,002,562 | A | 3/1991 | Oberlander |
| 5,002,563 | A | 3/1991 | Pyka et al. |
| 5,007,921 | A | 4/1991 | Brown |
| 5,026,391 | A | 6/1991 | McQueen et al. |
| 5,156,609 | A | 10/1992 | Nakao et al. |
| 5,171,252 | A | 12/1992 | Friedland |
| 5,192,303 | A | 3/1993 | Gatturna et al. |
| 5,246,443 | A | 9/1993 | Mai |
| 5,282,829 | A | 2/1994 | Hermes |
| 5,364,406 | A | 11/1994 | Sewell, Jr. |
| 5,370,685 | A | 12/1994 | Stevens |
| 5,464,416 | A | 11/1995 | Steckel |
| 5,573,543 | A | 11/1996 | Akopov et al. |
| 5,618,311 | A | 4/1997 | Gryskiewicz |
| 5,660,188 | A | 8/1997 | Groiso |
| 5,716,370 | A * | 2/1998 | Williamson et al. ......... 606/153 |
| 5,720,755 | A | 2/1998 | Dakov |
| 5,725,554 | A | 3/1998 | Simon et al. |
| 5,779,707 | A | 7/1998 | Bertholet et al. |
| 5,785,713 | A | 7/1998 | Jobe |
| 5,860,992 | A | 1/1999 | Daniel et al. |
| 5,891,160 | A | 4/1999 | Williamson, IV et al. |
| 5,902,310 | A | 5/1999 | Foerster et al. |
| 5,908,428 | A | 6/1999 | Scirica et al. |
| 5,921,997 | A | 7/1999 | Fogelberg et al. |
| 5,941,890 | A | 8/1999 | Voegele et al. |
| 5,957,940 | A | 9/1999 | Tanner et al. |
| 5,976,183 | A | 11/1999 | Ritz |
| 6,001,110 | A | 12/1999 | Adams |
| 6,042,607 | A | 3/2000 | Williamson, IV et al. |
| 6,059,787 | A | 5/2000 | Allen |
| 6,074,401 | A | 6/2000 | Gardiner et al. |
| 6,113,611 | A | 9/2000 | Allen et al. |
| 6,149,658 | A | 11/2000 | Gardiner et al. |
| 6,152,935 | A | 11/2000 | Kammerer et al. |
| 6,162,233 | A * | 12/2000 | Williamson et al. ......... 606/142 |
| 6,165,183 | A | 12/2000 | Kuehn et al. |
| 6,203,553 | B1 | 3/2001 | Robertson et al. |
| 6,220,248 | B1 | 4/2001 | Voegele et al. |
| 6,241,765 | B1 | 6/2001 | Griffin et al. |
| 6,248,117 | B1 | 6/2001 | Blatter |
| 6,334,446 | B1 | 1/2002 | Beyar |
| 6,348,054 | B1 | 2/2002 | Allen |
| 6,358,556 | B1 | 3/2002 | Ding et al. |
| 6,371,983 | B1 | 4/2002 | Lane |
| 6,402,780 | B2 | 6/2002 | Williamson, IV et al. |
| 6,432,064 | B1 | 8/2002 | Hibner et al. |
| 6,447,524 | B1 | 9/2002 | Knodel et al. |
| 6,514,265 | B2 | 2/2003 | Ho et al. |
| 6,551,332 | B1 | 4/2003 | Nguyen et al. |
| 6,607,542 | B1 | 8/2003 | Wild |
| 6,626,899 | B2 * | 9/2003 | Houser et al. ................. 606/14 |
| 6,638,297 | B1 | 10/2003 | Huitema |
| 6,641,593 | B1 | 11/2003 | Schaller et al. |
| 6,676,671 | B2 | 1/2004 | Robertson et al. |
| 6,702,826 | B2 * | 3/2004 | Liddicoat et al. ............ 606/151 |
| 2002/0035361 | A1 | 3/2002 | Houser et al. |
| 2002/0042621 | A1 | 4/2002 | Liddicoat et al. |
| 2002/0058967 | A1 | 5/2002 | Jervis |
| 2002/0173793 | A1 | 11/2002 | Allen |
| 2003/0045902 | A1 | 3/2003 | Weadock |
| 2003/0208211 | A1 | 11/2003 | Kortenbach |
| 2004/0193191 | A1 | 9/2004 | Starksen et al. |
| 2005/0107871 | A1 * | 5/2005 | Realyvasquez et al. .... 623/2.11 |

FOREIGN PATENT DOCUMENTS

| | | |
|---|---|---|
| EP | 0 552 433 A1 | 11/1992 |
| EP | 0 552 433 B1 | 11/1992 |
| EP | 0 580 994 A1 | 6/1993 |
| EP | 0 580 994 B1 | 6/1993 |
| EP | 0641546 A | 3/1995 |
| EP | 0826340 A2 | 3/1998 |
| FR | 320731 | 4/1902 |
| GB | 2 359 024 A | 8/2001 |
| WO | WO 96/00820 A1 | 3/1996 |
| WO | WO 96/08208 A1 | 3/1996 |
| WO | WO 96/16603 | 6/1996 |
| WO | 9739688 A2 | 10/1997 |
| WO | 9858591 A | 12/1998 |
| WO | WO 01/10310 A1 | 2/2001 |
| WO | WO 01/58363 A1 | 8/2001 |
| WO | WO 02/080779 A1 | 10/2002 |
| WO | WO 03/003930 A1 | 1/2003 |
| WO | WO 03/053289 A1 | 7/2003 |

OTHER PUBLICATIONS

PCT Written Opinion for PCT/US2005/043503, Applicant: Arbor Surgical Technologies, Inc., Forms PCT/ISA/237, 7 pages.

European Patent Office, Supplemental Search Report and Office Action for European Patent Application No. 04816910.6, Jan. 11, 2007, 8 pages.

European Attorney for Applicant, Reponse to Office Action for European Patent Application No. 04816910.6, Jul. 20, 2007, 15 pages.

US Patent and Trademark Office, Office Action for U.S. Appl. No. 11/004,445, filed Feb. 1, 2007, 12 pages.

Attorney for Applicant, Amendment and Response to Office Action for U.S. Appl. No. 11/004,445, filed Jul. 2, 2007, 22 pages.

* cited by examiner

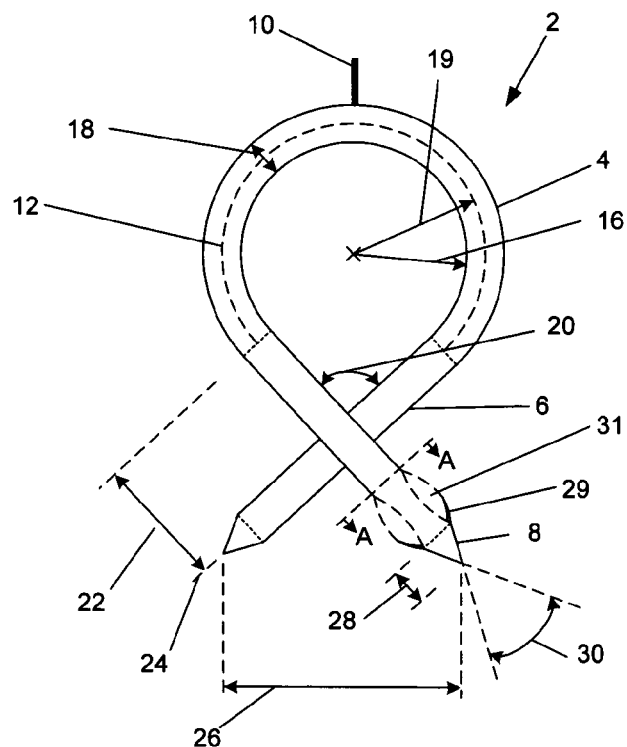
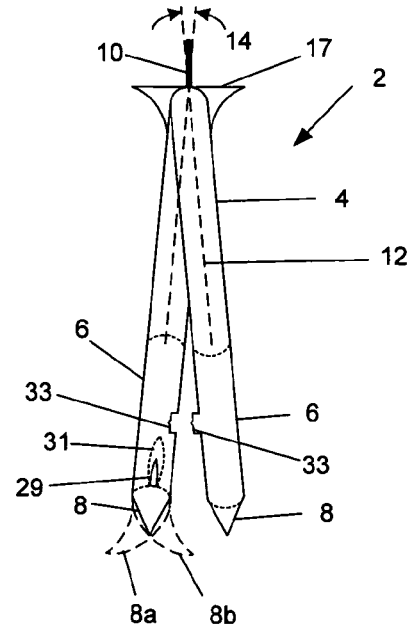
Fig. 2
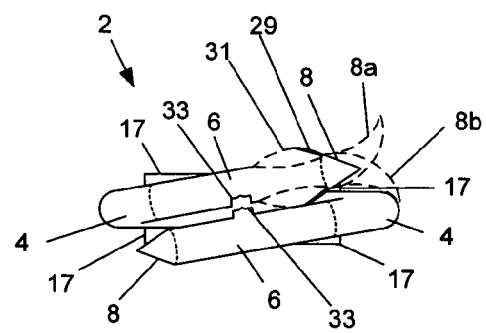
Fig. 3
Fig. 1

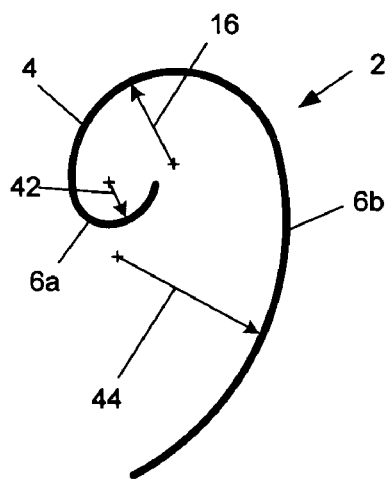
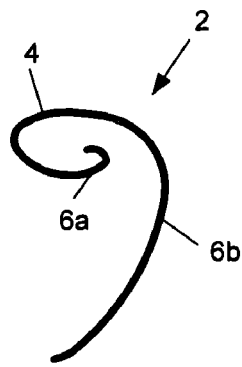
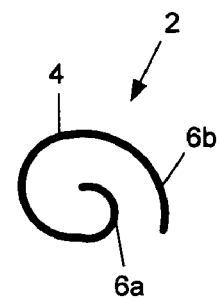
Fig. 15
Fig. 16
Fig. 17
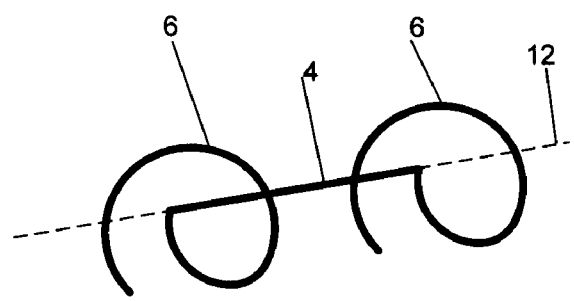
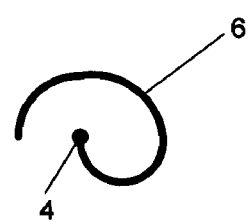
Fig. 18
Fig. 19

ATTACHMENT DEVICE AND METHODS OF USING THE SAME

BACKGROUND OF THE INVENTION

1. Field of the Invention

The present invention relates generally to a device for attaching a first mass to a second mass and methods of making and using the same.

2. Description of the Prior Art

Prosthetic heart valves can replace defective human valves in patients. Prosthetic valves commonly include sewing rings, suture cuffs or rings that are attached to and extend around the outer circumference of the prosthetic valve orifice.

In a typical prosthetic valve implantation procedure, the aorta is incised and the defective valve is removed leaving the desired placement site that may include a fibrous tissue layer or annular tissue. Known heart valve replacement techniques include individually passing sutures through the fibrous tissue or desired placements site within the valve annulus to form an array of sutures. Free ends of the sutures are extended out of the thoracic cavity and laid, spaced apart, on the patient's body. The free ends of the sutures are then individually threaded through a flange of the sewing ring. Once all sutures have been run through the sewing ring (typically 12 to 18 sutures), all the sutures are pulled up taught and the prosthetic valve is slid or "parachuted" down into place adjacent the placement site tissue. The prosthetic valve is then secured in place by traditional knot tying with the sutures. This procedure is time consuming as doctors often use three to ten knots per suture.

The sewing ring is often made of a biocompatible fabric through which a needle and suture can pass. The prosthetic valves are typically attached to the sewing rings which are sutured to a biological mass that is left when the surgeon removes the existing valve from the patient's heart. The sutures are tied snugly, thereby securing the sewing ring to the biological mass and, in turn, the prosthetic valve to the heart.

During heart valve replacement procedures, the patient is on heart-lung bypass which reduces the patient's oxygen level and creates non-physiological bloodflow dynamics. The longer a patient is on heat-lung bypass, the greater the risk for permanent health damage. Existing suturing techniques extend the duration of bypass and increase the health risks due to heart-lung bypass. Furthermore, the fixturing force created by suturing varies significantly from suture to suture, even for the same medical professional.

In addition, sutures and other attachment devices are used in a variety of medical applications where the use of the device of the present invention would provide an advantage in fixing a first mass to a second mass, where the first mass is a tissue or a device or prosthesis, and the second mass is a tissue or a device or prosthesis. These applications include anchoring a prosthesis such as a synthetic or autologous graft to surrounding tissue or another prosthesis, tissue repair such as in the closure of congenital defects such as septal heart defects, tissue or vessel anastomosis, fixation of tissue with or without a reinforcing mesh for hernia repair, orthopedic anchoring such as in bone fusing or tendon or muscle repair, ophthalmic indications, laparoscopic or endoscopic tissue repair or placement of prostheses, or use by robotic devices for procedures performed remotely.

For these indications and others, there is a need for a fixturing device to minimize the time spent fixturing certain devices or conduits, such as a valve prosthesis and a second mass, a vessel to another vessel or anatomical structure, tissue to tissue, surrounding tissue to a second prosthesis, and the like as described above. Furthermore, there is a need for a device that compliments existing suturing or attachment devices and methods and reduces fixturing times. Also, there is a need for a fixturing device that can be easily removed. There also exist a need to provide a fixturing device that can provide a consistent fixturing force.

BRIEF SUMMARY OF THE INVENTION

A device for connecting a first mass to a second mass is disclosed. The device has a base and a first leg. The base has a base axis, a first end and a second end. The first leg extends from the first end of the base. The device has a first configuration and a second configuration. When the base is rotated with respect to the base axis, the device is in the first configuration. The device can also have a second leg extending from the second end of the base.

Another device for connecting a first mass to a second mass is disclosed. The device has a base, a first leg and a second leg. The base has a base axis, a first end and a second end. The first leg has a first longitudinal axis and a first leg length. The first leg extends from the first end of the base. The second leg has a second longitudinal axis and a second leg length. The second leg extends from the second end of the base. The first leg length is substantially longer than the second leg length.

The device can have a first configuration and a second configuration. When the base is rotated with respect to the base axis, the device is in the first configuration.

Yet another device for connecting a first mass to a second mass is disclosed. The device has a base, a first leg and a second leg. The base is curved. The base has a base diameter, a first end and a second end. The first leg has a first longitudinal axis and a first leg length. The first leg extends from the first end of the base. The second leg has a second longitudinal axis and a second leg length. The second leg extends from the second end of the base. The device has a relaxed configuration. In the relaxed configuration the first leg crosses the second leg at a leg angle. The leg angle is less than 180 degrees.

The leg angle can be less than or equal to 90 degrees. The leg angle can be less than or equal to 60 degrees. The base diameter can be less than or equal to 0.13 inches. The base diameter can be greater than or equal to 0.08 inches.

A method of attaching a first mass to a second mass is disclosed. The method uses an attachment device having a base, a first leg, and a second leg. The base has a first end and a second end. The first leg extends from the first end of the base. The second leg extends from the second end of the base. The attachment device has a first configuration and a second configuration. The method includes holding the attachment device in the first configuration. The method also includes twisting the base of the attachment device to force the attachment device into the second configuration. Further, the method includes inserting the attachment device into the first mass and the second mass. The method also includes releasing the attachment device.

Twisting the base of the attachment device can occur before inserting the attachment device into the first mass. Inserting the attachment device, at least partially, into the first mass can occur before twisting the base of the attachment device.

Another method of attaching a first mass to a second mass is disclosed. The method includes forcibly holding an attachment device in a second configuration. The attachment device has a first configuration and the second configuration. The method also includes inserting the attachment device into the first mass and the second mass. The method also includes releasing the attachment device into the first configuration.

BRIEF DESCRIPTION OF THE DRAWINGS

FIG. 1 is a front view of an embodiment of the attachment device.

FIG. 2 is a side view of an embodiment of the attachment device.

FIG. 3 is a bottom view of an embodiment of the attachment device.

FIGS. 14 and 15 are front views of various embodiments of the attachment device.

FIG. 16 is a front perspective view of an embodiment of the attachment device.

FIG. 17 is a top view of the embodiment of the attachment device shown in FIG. 16.

FIG. 18 is a side perspective view of an embodiment of the attachment device.

FIG. 19 is a side view of the attachment device shown in FIG. 18.

DETAILED DESCRIPTION

Figure 4:
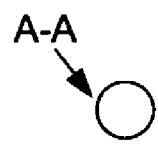
FIGS. 4-10 illustrate embodiments of section A-A of the attachment device.
Figure 5:
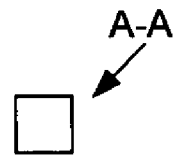
Figure 6:
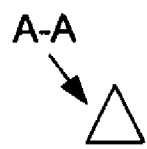
Figure 7:
Figure 8:
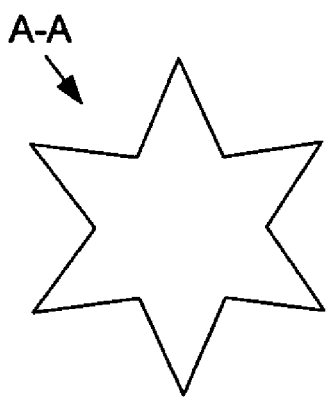

FIGS. 1 through 3 illustrate an attachment device 2. The attachment device 2 can have a base 4, legs 6, and a tip 8 at the end of each leg 6. (Phantom lines delineate the base 4, legs 6 and tips 8.) The base 4, legs 6 and tips 8 can be separate or integral elements. A flag 10 can be attached to, and extend from, the base 4. The base 4 and/or the legs 6 can be straight or curved.

The attachment device 2 can be made from a deformable or elastic material or a combination of materials having resulting deformable or elastic properties. The material can be, for example, stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), polymers such as polyester (e.g., DACRON® from E.I. Du Pont de Nemours and Company, Wilmington, Del.), polypropylene, polytetrafluoroethylene (PTFE), expanded PTFE (ePTFE), polyether ether ketone (PEEK), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), extruded collagen, silicone, echogenic, radioactive, radiopaque materials or combinations thereof. Examples of radiopaque materials are barium sulfate, titanium, stainless steel, nickel-titanium alloys, tantalum and gold.

Any or all elements of the attachment device 2 can be a matrix for cell ingrowth or used with a fabric, for example a covering (not shown) that acts as a matrix for cell ingrowth. The fabric can be, for example, polyester (e.g., DACRON® from E.I. du Pont de Nemours and Company, Wilmington, Del.), polypropylene, PTFE, ePTFE, nylon, extruded collagen, silicone or combinations thereof.

The attachment device 2 and/or the fabric can be filled and/or coated with an agent delivery matrix known to one having ordinary skill in the art and/or a therapeutic and/or diagnostic agent. These agents can include radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and *Chlamydia Pneumoniae, Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

A base axis 12 can extend longitudinally through the transverse cross-sectional center of the base 4. As shown in FIG. 2, when viewed from the side, the base axis 12 can form a base plane angle 14 from about 0° to about 30°, for example about 10°. The base 4 can have a base inner radius 16 from about 0.25 mm (0.010 in.) to about 19.1 mm (0.750 in.), for example about 1.91 mm (0.075 in.). The proximal end of the base 4 can be formed into a table 17. The table 17 can be a flat surface that tapers to the base 4.

The base 4 and legs 6 can have a shaft diameter 18 from about 0.03 mm (0.001 in.) to about 6.35 mm (0.250 in.), for example, about 0.51 mm (0.020 in.). The base 4 and legs 6 can have the same or different shaft diameters 18. A base neutral radius 19 can be the base inner radius 16 and half the shaft diameter 18. As shown in FIG. 1, the legs 6 can intersect at a leg angle 20 in or near the plane of the attachment device 2 or in or near the approximate plane of the base 4. An approximate plane is a plane that can be used whether the base 4 does or does not fall on a flat plane. If the base 4 is a straight line or a point, the approximate plane of the base 4 can be calculated using the points of the legs 6 that are nearest the base 4 and out of line with the base 4. The leg angle 20 can be from about 180° to about 10°, more narrowly from about 90° to about 60°, for example about 45° or, for example, about 60°.

The length from an end of the base 4 to a longitudinal leg axis 24 can be a body length 22. The body length 22 can be from about 0.25 mm (0.010 in.) to about 12.7 mm (0.500 in.), for example about 2.913 mm (0.1147 in.). The length between the distal end of one tip 8 and the distal end of the opposite tip 8 can be a tip distance 26. The tip distance 26 can be from about 0.03 mm (0.001 in.) to about 25.4 mm (1.000 in.), more narrowly about 1.3 mm (0.050 in.) to about 3.18 mm (0.125 in.), for example about 2.3 mm (0.090 in.).

The tip 8 can have a tip length 28 from about 0.05 mm (0.002 in.) to about 12.7 mm (0.500 in.), for example about 1.0 mm (0.040 in.). The tip 8 can have a tip angle 30 from about 50 to about 90°, for example about 30°. The tips 8 can be straight, pointed ends, curve out of line (shown by alternative tips 8a and 8b, drawn in phantom lines in FIGS. 2 and 3) from the nearest end of the leg 6, or combinations thereof.

The tips 8 and/or legs 6 can have retention devices 29. The retention devices 29 can be barbs, spikes, hooks, threads, ribs, splines, a roughened surface, a sintered surface, a covered surface (e.g., with DACRON® from E.I. du Pont de Nemours and Company, Wilmington, Del.) or combinations thereof. A retention coating 31, for example a biodegradable coating or filler such as gel or gelatin or otherwise removable, can be on and/or around and/or near the retention devices 29. The retention coating 31 (shown in phantom lines) can be configured to render the retention device 29 substantially ineffective until a substantial amount of the retention coating 31 has been biodegraded or otherwise removed.

The legs 6 can have mechanical interfaces 33, for example, a slot, snap, protrusion, latch, catch or combinations thereof. The interfaces 33 can be aligned so the interface on one leg 6 meets the interface 33 on the other leg 6 at the point where the legs 6 cross. The interfaces 33 can removably attach to each other.

Figure 9:
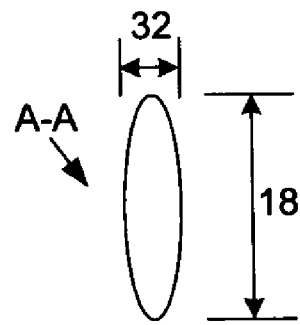

FIGS. 4 through 10 illustrate examples of cross-section A-A of the legs 6 and/or the base 4. The cross-section A-A of the legs 6 can be the same or different as the cross-sections of the base 4. The cross-sections of the base 4 and/or legs 6 can be constant or vary along their respective lengths. FIGS. 4 through 8, respectively, illustrate circular, rectangular (including square), triangular, substantially flat, and star-David shaped or irregular cross-sections A-A. FIG. 9 illustrates an oval cross-section A-A. A ratio of the shaft diameter 18 to the length of a minor axis 32 can be from about 1:1 to about 20:1, for example 10:1.

Figure 10:
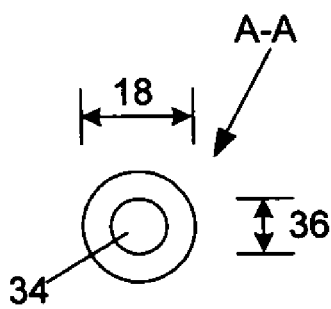

FIG. 10 illustrates a cavity 36 inside the cross-section A-A. The cavity 34 can be hollow or can be filled completely or partially. The cavity 34 can be filled with an agent delivery matrix known to one having ordinary skill in the art and/or a therapeutic and/or diagnostic agent and/or echogenic and/or radioactive and/or radiopaque materials, for example, the agents and/or materials listed supra. The type and amount of filling can vary along the length of the base 4 and/or legs 6. The ratio of the shaft diameter 18 to a cavity diameter 36 can be from about 1:1 to about 50:1, for example, about 2:1.

Figure 11:
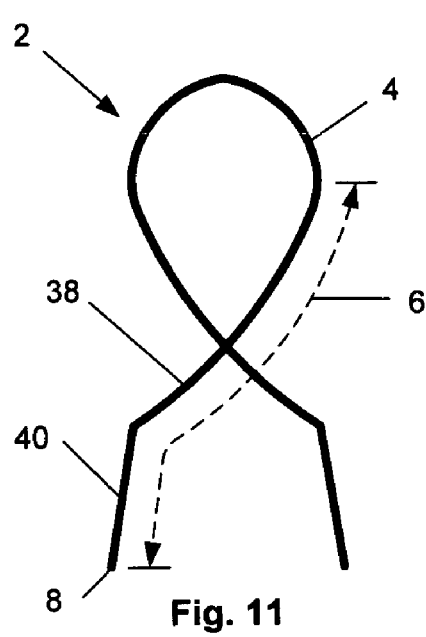
FIG. 11 is a front view of an embodiment of the attachment device.
Figure 12:
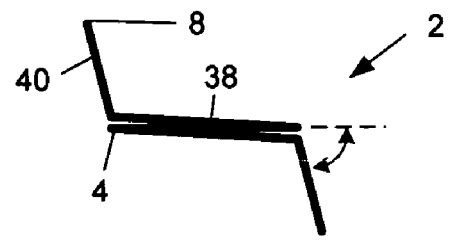
FIGS. 12 and 13 are bottom views of various embodiments of the attachment device shown in FIG. 11.
Figure 13:
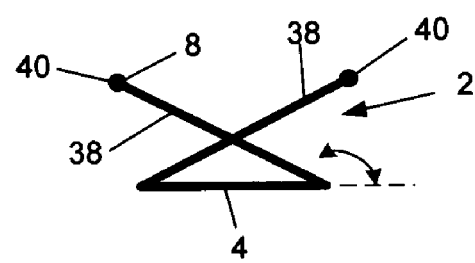

FIG. 11 illustrates an attachment device 2 that can have a leg 6 that can have a first leg segment 38 and a second leg segment 40. The first leg segment 38 can extends from the base 4. The second leg segment 40 can extend on a proximal end from the first leg segment 38. The tip 8 can extend from a distal end of the second leg segment 40. The second leg segment 40 can have a different radius of curvature than the first leg segment 38 and/or form an angle with respect to the first leg segment 40. FIG. 12 illustrates that the second leg segment 40 can form an angle (shown by arrows) with the approximate plane of the base 4. FIG. 13 illustrates that the first leg segment 38 can form an angle (shown by arrows) with the approximate plane of the base 4. The second leg segments 40 can be substantially parallel with the approximate plan of the base 4.

Figure 14:
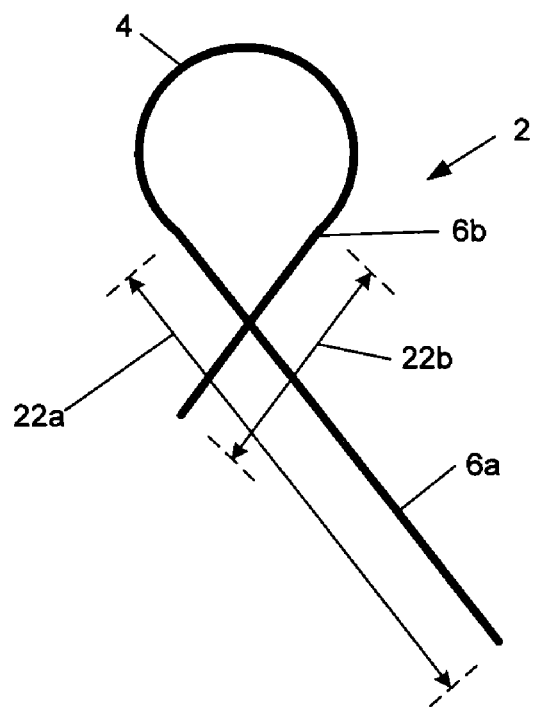

FIG. 14 illustrates an attachment device 2 that can have a first leg 6a that can be substantially longer than a second leg 6b. The ratio of a first leg-tip length 22a to a second leg-tip length 22b can be from about 1:1 to about 10:1, for example, about 3:1.

FIG. 15 illustrates an attachment device that can have a first leg radius 42 and a second leg radius 44. The ratio of the first leg radius 42 to the second leg radius 44 can be from about 1:1 to about 50:1, for example about 10:1.

FIGS. 16 and 17 illustrate an attachment device 2 that can have a "flat top." The approximate plane of the second leg 6b can form an angle, for example about 90°, with the approximate plane of the base 4. When in use, the flat top can further anchor the attachment device 2 against the first mass and/or second mass. FIGS. 18 and 19 illustrate an attachment device 2 that can have arms 6 that can wrap around the base axis 12.

Figure 20:
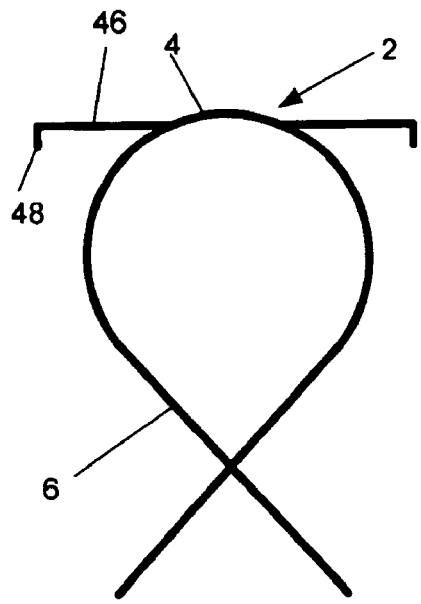
FIGS. 20 and 21 are front views of various embodiments of the attachment device.
Figure 21:
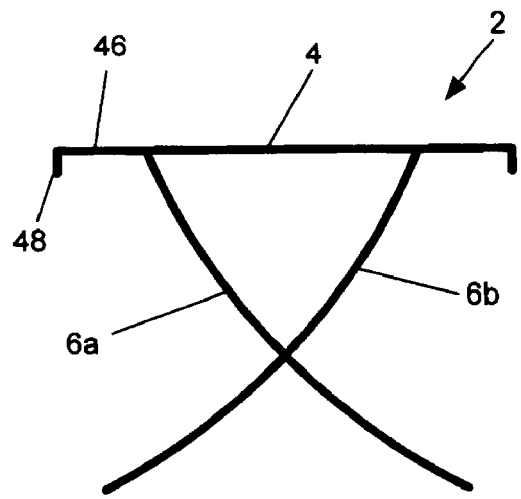

FIG. 20 illustrates an attachment device 2 that can have arms 46 that can extend from the base 4 and/or the legs 6. When deployed, the arms 46 can squeeze tissue between the arms 46 and the legs 6 and/or base 4 for additional retention force. Anchors 48 can extend from the arms 46, for example at the distal ends of the arms 46. The anchors 48 can be, for example, hooks, barbs, spikes, staples or combinations thereof. The anchors 48 can extend directly from the base 4 and/or legs 6 with or without arms 46 separately attached to the base 4 and/or legs 6. FIG. 21 illustrates an attachment device 2 that can have a straight base 4 and can have the arms 46 extending from the base 4.

Figure 22:
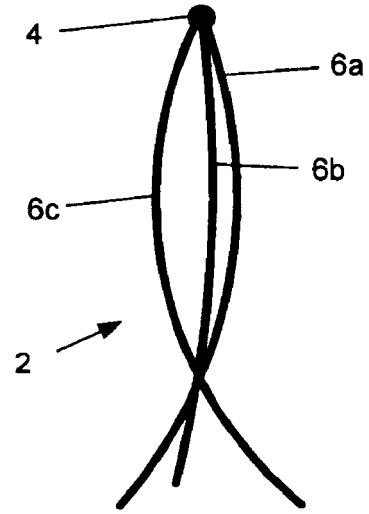
FIG. 22 is a front perspective view of an embodiment of the attachment device.
Figure 23:
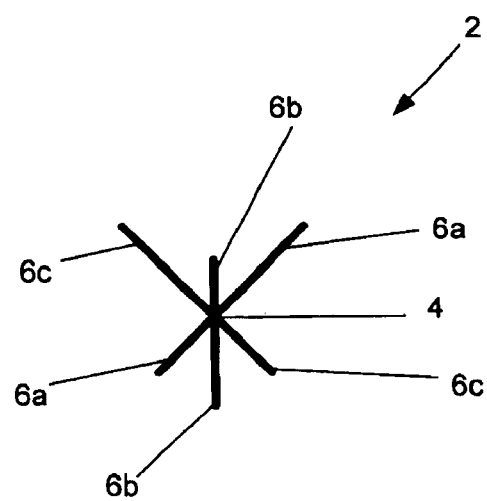
FIG. 23 is a top view of the embodiment of the attachment device shown in FIG. 22.

FIGS. 22 and 23 illustrate an attachment device that can have first, second and third legs 6a, 6b and 6c. The base 4 can be a platform, wireframe, or point attachment which can be spot-welded or brazed, tube crimped or otherwise mechanically connected. The planes of the legs 6a, 6b and 6c can intersect at substantially equal angles, about 120°, or unequal angles.

Figure 24:
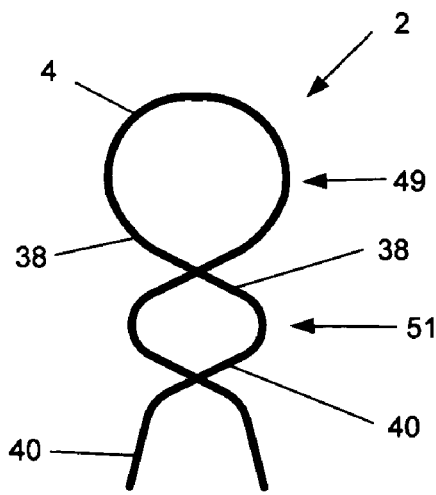
FIG. 24 is a front view of an embodiment of the attachment device.

FIG. 24 illustrates an attachment device that can have a first loop 49 and a second loop 51. The first loop 49 can be formed from the base 4 and a proximal portion of the first leg segments 38. The second loop 51 can be formed from a distal portion of the first leg segments 38 and a proximal portion of the second leg segments 40.

Methods of Making

Figure 25:
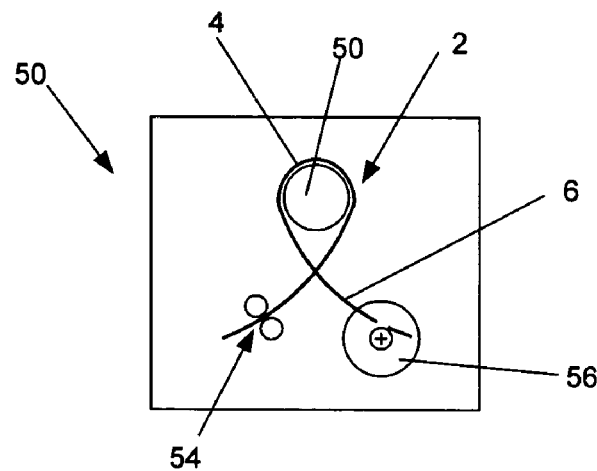
FIG. 25 illustrates an embodiment of a mandrel for manufacturing the attachment device.

FIG. 25 illustrates a mandrel 50 that can be used to form the attachment device 2, for example during heat treatment. The base 4 and/or legs 6 can be held on the mandrel 50 by a single cylinder 52, a formed path 54, a pressure plate 56, for example a washer under a screw or combinations thereof. Methods for forming shape memory alloys (e.g., Nitinol) are known to those having ordinary skill in the art. The tips 8 can be formed, for example, by grinding, electropolishing, or precision sharpening (e.g., polishing services from Point Technologies, Inc., Boulder, Colo.) to a satisfactory geometry, including a trocar point, beveled, rounded, tapered, pointed or flattened.

Other methods known to one having ordinary skill in the art can be used to manufacture the attachment device 2 and/or its elements. For example, manufacturing techniques include molding, machining, casting, forming (e.g., pressure forming), crimping, stamping, melting, screwing, gluing, welding, die cutting, laser cutting, electrical discharge machining (EDM), etching or combinations thereof.

Any elements, sub-assemblies, or the attachment device 2 as a whole after final assembly, can be coated by dip-coating or spray-coating methods known to one having ordinary skill in the art, utilizing materials such as PTFE (e.g., TEFLON® from E.I. du Pont de Nemours and Company, Wilmington, Del.), polyester (e.g., DACRON® from E.I. du Pont de Nemours and Company, Wilmington, Del.), gelatin, gel, other polymers or combinations thereof. One example of a method used to coat a medical device for vascular use is provided in U.S. Pat. No. 6,358,556 by Ding et al. and hereby incorporated by reference in its entirety. Time release coating methods known to one having ordinary skill in the art can also be used to delay the release of an agent in the coating. The coatings can be thrombogenic or anti-thrombogenic.

The attachment device 2, or any element thereof (e.g., the base 4) can be covered with a fabric, for example polyester (e.g., DACRON® from E.I. du Pont de Nemours and Company, Wilmington, Del.), polypropylene, PTFE (e.g., TEFLON® from E.I. du Pont de Nemours and Company, Wilmington, Del.), ePTFE, nylon, extruded collagen, gel, gelatin, silicone or combinations thereof. Methods of covering an implantable device with fabric are known to those having ordinary skill in the art, for example, sintering, spray coating, adhesion, loose covering, dipping or combinations thereof.

Methods of Using

The attachment device 2 can have a first configuration (e.g., the configuration shown in FIGS. 26 and 27) and a second configuration (e.g., the configuration shown in FIGS. 1 through 3). The attachment device 2 can have the second configuration when the attachment device is in a relaxed state, with no external forces applied (e.g., prior to insertion or use). The attachment device 2 can have the first configuration when external forces are applied, such as by a delivery tool prior to delivery. When external forces are removed from the attachment device 2, the attachment device 2 can revert from the first configuration to the second configuration.

The attachment device can substantially revert to the second configuration even when some permanent hysteresis deformation occurs and/or when a foreign object (e.g., a first and/or second mass) is obstructing the attachment device 2. When the attachment device 2 has the first configuration, one or both legs 6 can be rotated with respect to the base 4 (e.g., by rotating the base 4 around the base axis 12, one or both legs 6 splay or separate as they are torqued by the twisting or rotating around of the base).

Figure 26:
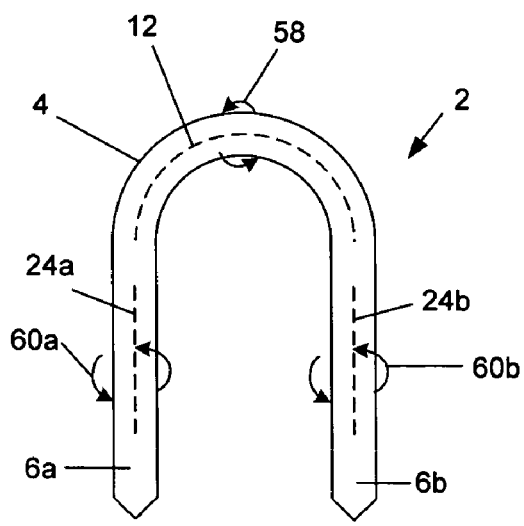
FIGS. 26 and 27 illustrate methods of changing the attachment device from a first configuration to a second configuration.

FIG. 26 illustrates a method of forcing the attachment device to have the first configuration. The attachment device 2 can be forced to have the first configuration by the application of a base torque, shown by arrows 58, applied about the base axis 12. The base torque can be directly applied to the base 4. The base torque indirectly becomes, or can be applied as, a leg torque, as shown by arrows 60a and 60b, to the legs 6a and/or 6b about the leg axes 24a and 24b. If approximately two times the base neutral radius 19 is less than the tip distance 26, the legs 6 will splay outward when entering the first mass 68. If approximately two times the base neutral radius 19 is greater than or equal to the tip distance 26, the legs 6 will splay inward or stay vertical when deploying into the first mass 68.

Figure 27:
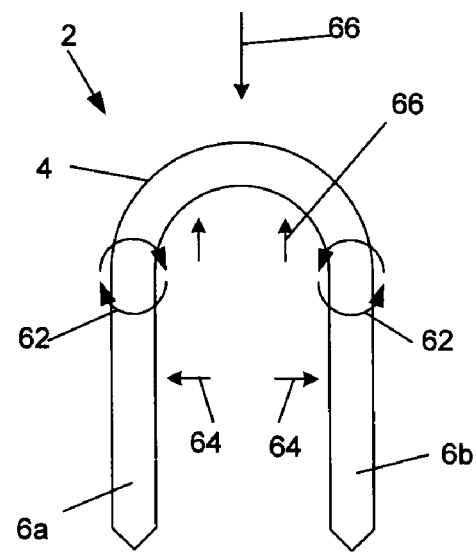

FIG. 27 illustrates a method of forcing the attachment device to have the first configuration. The attachment device 2 can be forced to have the first configuration by the application of a pivot torque, shown by arrows 62, applied about the area where the base 4 attaches to the legs 6, so that the legs 6 are forced to pivot radially outward from each other. The pivot torque can be applied by applying outward translational forces, as shown by arrows 64, to one or both legs 6. The pivot torque can be applied by applying translational forces to the base 4, as shown by arrows 66.

Figure 28:
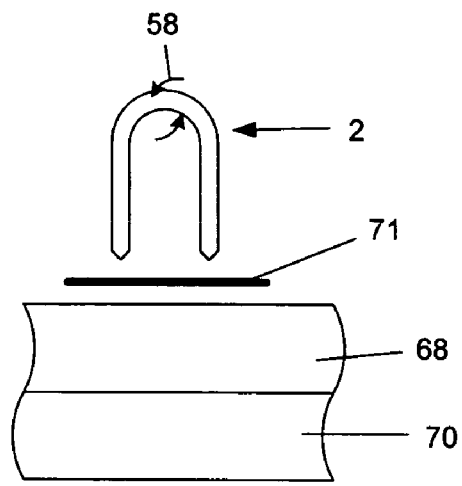
FIGS. 28-30 are cross-sections illustrating an embodiment of a method of using the attachment device.
Figure 29:
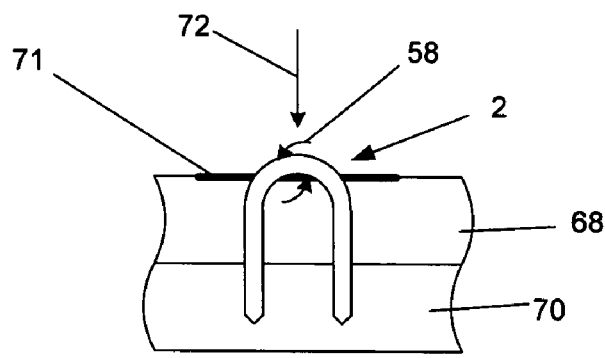
Figure 30:
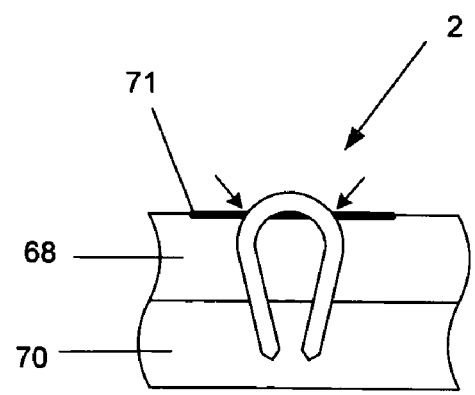

As illustrated in FIGS. 28 through 30, the attachment device 2 can be deployed to attach a first mass 68 to a second mass 70. The first mass 68 and/or the second mass 70 can be a prosthesis and/or a tissue, or both tissue or both prostheses. The prosthesis can be, for example, cardiac leads, markers, stents, grafts, stent-grafts, heart valves, annuloplasty rings, autografts, allografts, xenografts or any assemblies thereof or combination thereof. The tissue can be, for example, vessels, valves, organs (e.g., intestine, heart, skin, liver, kidney, urethra, bone mass, tendon, nerve, muscle), calcified soft tissue or any combination thereof.

Heart valve assemblies disclosed by Griffin et al. in U.S. Pat. No. 6,241,765, by Lane in U.S. Pat. No. 6,371,983 and by Ritz in U.S. Pat. No. 5,976,183, both of which are hereby incorporated in their entireties, can be placed with the use of the device of the present invention. Other heart valve assemblies that can be used include, for example, the Advantage Bileaflet heart valve, Parallel valve, Freestyle stentless aortic valve, Hancock Porcine heart valve, Hancock apical left ventricular connector model 174A, Hancock valved conduit models 100, 105, 150, Hall Medtronic heart valve, Hall Medtronic valved conduit, MOSAIC® heart valve and Intact porcine tissue valve (by Medtronic, Inc. Minneapolis, Minn.); Angelini Lamina-flo valve (by Cardio Carbon Company, Ltd., England); Bjork-Shiley single-disk, monostrut and caged-disk valves (Shiley, Inc., now-defunct, previously of CA); Wada-Cutter valve and Chitra Cooley-Cutter valve (by Cutter Biomedical Corp., San Diego, Calif.); Angioflex trileaflet polyurethane valve (by Abiomed, Inc., Danvers, Mass.); ATS AP Series heart valve and ATS Standard heart valve (by ATS Medical, Inc., Minneapolis, Minn.); ANNU-LOFLO® annuloplasty ring, ANNUFLEX® annuloplasty ring, CARBSEAL® valved conduit, ORBIS® Universal aortic and mitral valve, pediatric/small adult valve, R series valve, SUMIT® mitral valve, TOP HAT® aortic valve, OPTI-FORM® mitral valve, MITROFLOW SYNERGY® PC stented aortic pericardial bioprosthesis and the SYNERGY® ST stented aortic and mitral porcine bioprosthesis (by Carbo-Medics, Inc., Austin, Tex.); ON-X® prosthetic heart valve (by MCRI®, LLC, Austin, Tex.); Starr-Edwards SILAS- TIC® ball valve, Starr-Edwards 1000, Starr-Edwards 1200, Starr-Edwards 1260, Starr-Edwards 2400, Starr-Edwards 6300, Starr-Edwards 6500, Starr-Edwards 6520, Carpentier-Edwards porcine tissue valve, Carpentier-Edwards pericardial prosthesis, Carpentier-Edwards supra-annular valve, Carpentier-Edwards annuloplasty rings, Duromedics valve and PERIMOUNT® heart valve (by Edwards Lifesciences Corp., Irvine, Calif.); Cross-Jones Lenticular disc valve (by Pemco, Inc.); Tissuemed stented porcine valve (by Tissuemed, Ltd., Leeds, England); Tekna valve (by Baxter Healthcare, Corp., Deerfield, Ill.); Komp-01 mitral retainer ring (by Jyros Medical Ltd., London, England); SJM® Masters Series mechanical heart valve, SJM® Masters Series aortic valved graft prosthesis, ST. JUDE MEDICAL® mechanical heart valves, ST. JUDE MEDICAL® mechanical heart valve Hemodynamic Plus (HP) series, SJM REGENT® valve, TORONTO SPV® (Stentless Porcine Valve) valve, SJM BIOCOR® valve and SJM EPIC® valve (St. Jude Medical, Inc., St. Paul, Minn.); Sorin Bicarbon, Sorin Carbocast, Sorin Carboseal Conduit, Sorin Pericarbon and Sorin Pericarbon Stentless (by Snia S.p.A., Italy). The attachment devices of the present invention may be deployed to implant these various devices in the supra-annular position, or infrannular, depending on the geometry and preferred placement of a particular device. Similarly, it may be advantageous to use the attachment devices 2 of the present invention to secure a sewing ring, or first prosthesis by placing them horizontally or vertically within or around the annulus of such ring, prior to placing a second prosthesis including a valve structure, as provided in U.S. application Ser. No. 10/646,639 filed, 22 Aug. 2003, hereby incorporated by reference in its entirety.

FIG. 28 illustrates that the attachment device 2 can be held in the first configuration. The attachment device 2 can be fed through a pledget 71 before the attachment device 2 is forced into the first mass 68. The pledget 71 can be a piece of fabric, for example, a fabric listed supra. The pledget 71 can be loaded onto the attachment device 2 before use. FIG. 29 illustrates that the attachment device 2 can be forced, as shown by arrow 72, into and through the first mass 68 and part of the second mass 70. FIG. 30 illustrates that the attachment device 2 can be released from having the first configuration. The attachment device 2 can revert to having substantially the second configuration. A pinching force, shown by arrows, can be applied to the attachment device 2 to encourage additional reversion of the attachment device 2 to having the second configuration. The attachment device 2 shown in FIG. 24 can be deployed in the same manner as described supra, except that the attachment device 2 shown in FIG. 24 can be rotated sufficiently to straighten the first and second loops, before or during deployment.

The attachment device 2 can be removed and redeployed at any stage of deployment supra, for example, if the surgeon is unsatisfied with the position of the attachment device 2, or if the prosthesis need replacing or "redoing" at a point in the future. If the attachment device 2 has a retention device 29, when the retention coating 31 sufficiently biodegrades or is otherwise removed, the retention devices 29 will become exposed and can substantially prevent the removal of the attachment device 2 from the deployment site. Removal may still be achieved however, by apply sufficient force (by a tool or other device) to overcome the strength of the secondary retention element.

Figure 31:
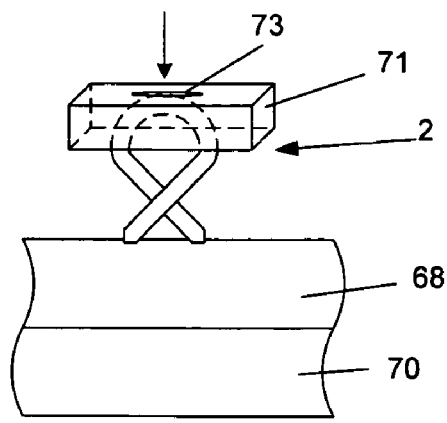
FIGS. 31-33 are cross-sections illustrating an embodiment of a method of using the attachment device with the pledget shown in full perspective for FIGS. 31 and 32.
Figure 32:
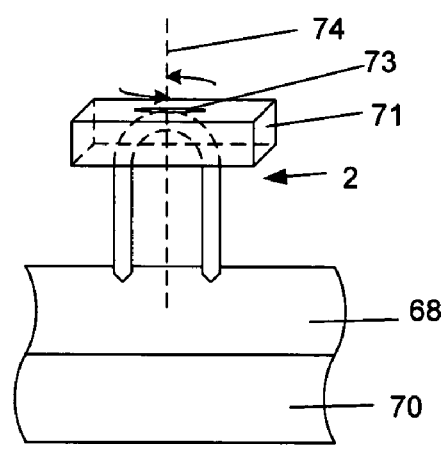
Figure 33:
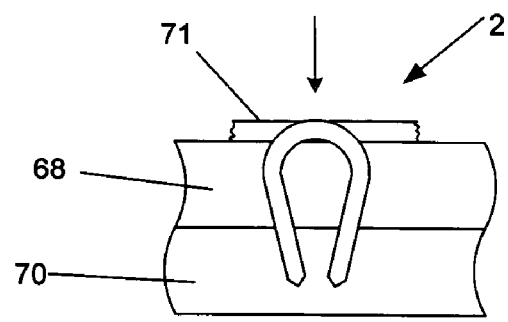

FIGS. 31 though 33 illustrate a method of deploying the attachment device 2 to attach a first mass 68 to a second mass 70. The pledget 71 can be fed over the attachment device 2 before use. The pledget 2 can be formed as a rectangular container with an access opening 73, for example a slit, hole, or aperture, to allow access to the base 4 of the attachment device 2. The attachment device 2 can have the second configuration. The attachment device 2 can be forced, as shown by arrow, so the tips 8 engage the first mass 68. FIG. 32 illustrates that, with the tips 8 held by the first mass 68, a longitudinal torque, shown by arrows, applied to the attachment device 2 about a longitudinal axis 74 can then force the attachment device 2 into the first configuration. As illustrated by FIG. 33, the attachment device 2 can be forced, shown by arrow, through the first mass 68 and part of the second mass 70. The longitudinal torque (not shown in FIG. 33) can be removed during deployment or after the attachment device 2 is completely deployed into the first and second masses 68 and 70. The pledget 71 can be crushed during deployment.

Figures 34, 35:
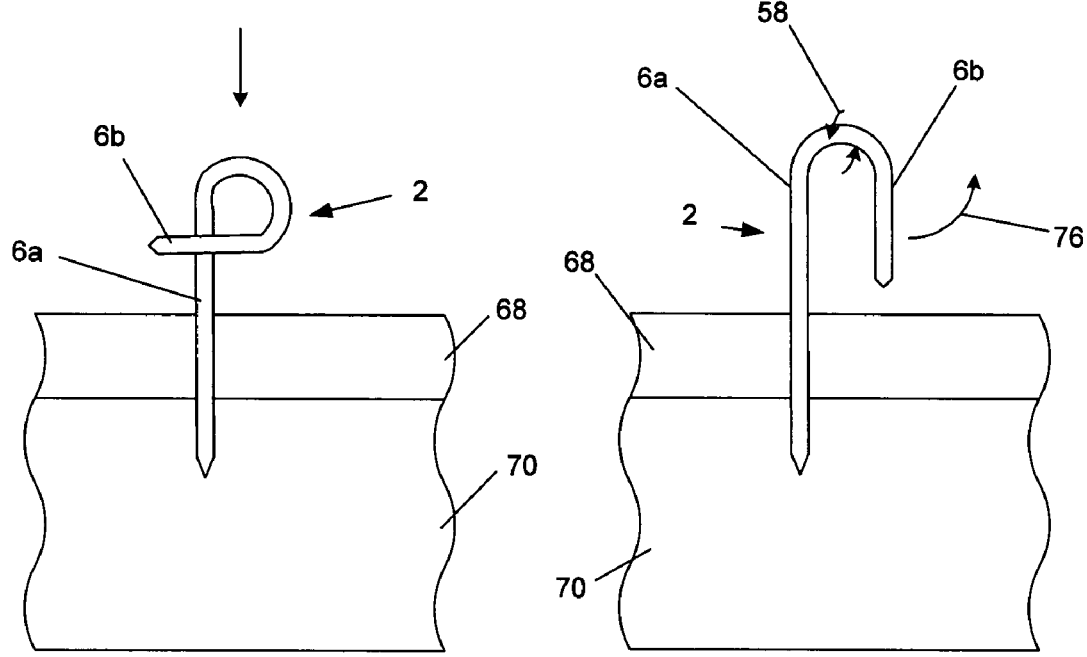
FIGS. 34-36 are cross-sections illustrating an embodiment of a method of using the embodiment of the attachment device shown in FIG. 14.
Figure 36:
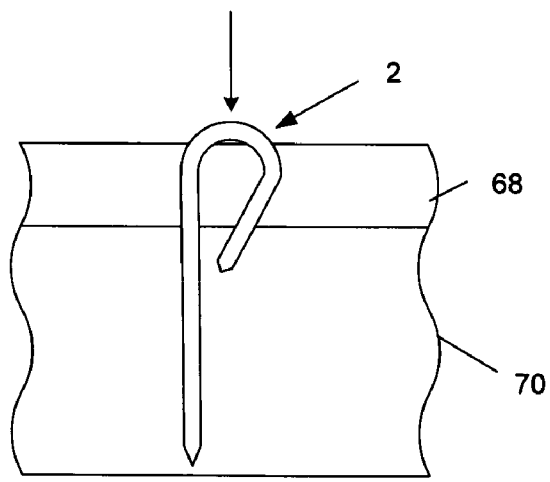

FIGS. 34 through 36 illustrate a method of deploying the attachment device shown in FIG. 14. The first leg 6a can be forced, as shown by arrow, into and through the first mass 68 and part of the second mass 70. The first leg 6a can have a "paddle" (not shown). The paddle can be a flat oval or long rectangular cross-sectional shape on one leg. The paddle can increase resistive force with the first and/or second mass 68 and/or 70 when applying torque to the attachment device 2.

FIG. 35 illustrates that the attachment device 2 can be forced into the first configuration by applying a base torque, shown by arrows 58. The second leg 6b can then rotate outwardly from the attachment device 2, as shown by arrow 76.

FIG. 36 illustrates that the attachment device 2 can be forced, shown by arrow, through the first mass 68 and part of the second mass 70. The base torque (not shown in FIG. 36) can be removed during deployment or after the attachment device 2 is completely deployed into the first and second masses 68 and 70.

Figure 37:
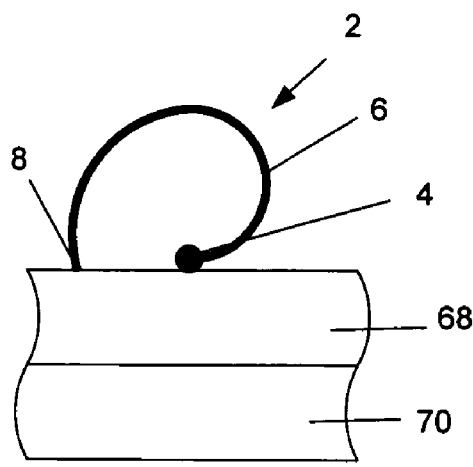
FIGS. 37-39 are cross-sections illustrating an embodiment of a method of using the embodiment of the attachment device shown in FIGS. 18 and 19.
Figure 38:
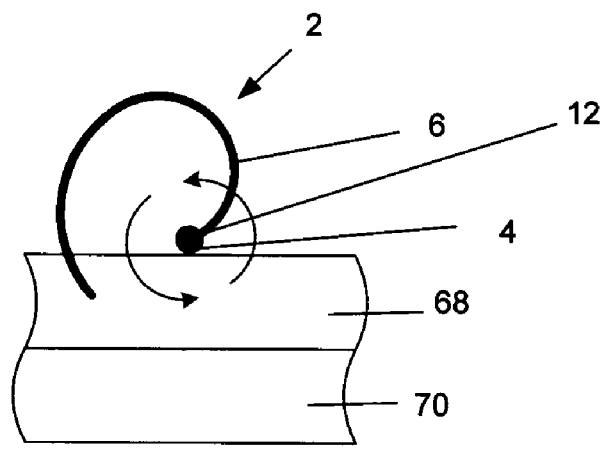
Figure 39:
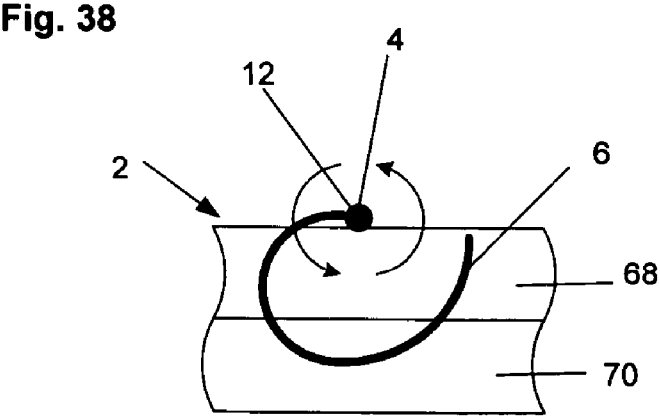

FIGS. 37 through 39 illustrate a method of deploying the attachment device 2 shown in FIGS. 18 and 19. FIG. 37 illustrates that the base 4 and the tips 8 can be placed in contact with or near the first mass 68. FIG. 38 illustrates that the arms 6 can be rotated, as shown by arrows, about the base axis 12. The arms 6 can be rotated to cause the arms 6 to be forced into the first mass 68. FIG. 39 illustrates that the arms 6 can be rotated, as shown by arrows, further about the base axis 12. The arms 6 can be forced into and through the second mass 70. The arms 6 can re-enter the first mass 68.

Figure 40:
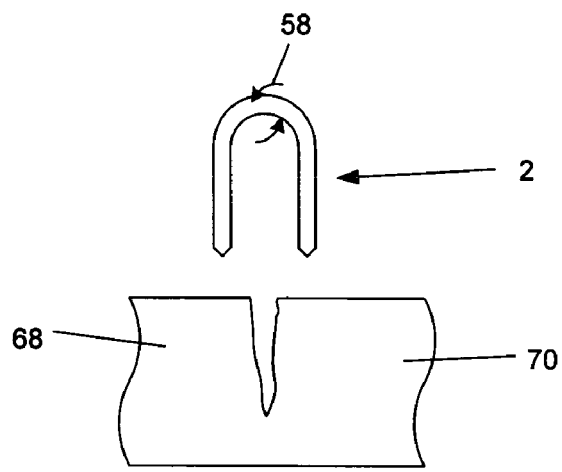
FIGS. 40-42 are cross-sections illustrating an embodiment of a method of using the attachment device.
Figure 41:
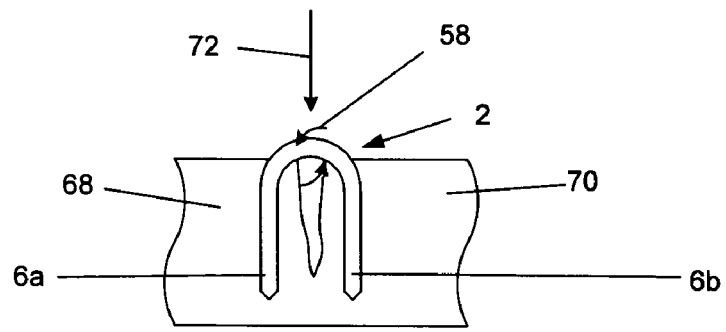
Figure 42:
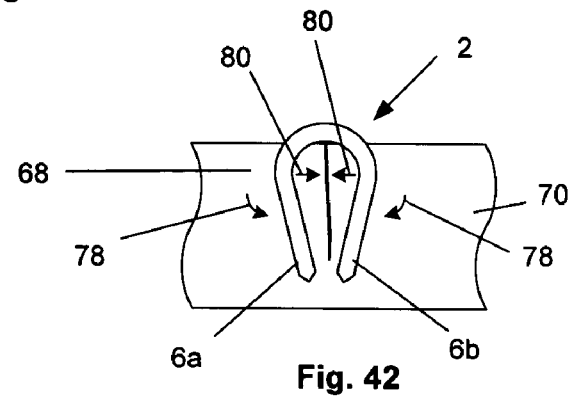

FIGS. 40 through 42 illustrate a method of deploying the attachment device 2 to attach a first mass 68 to a second mass 70. The first mass 68 and the second mass 70 can be two sections of the same object, such as when the attachment device 2 is used to close a wound. FIG. 40 illustrates that the attachment device 2 can be held in the first configuration. FIG. 41 illustrates that the attachment device 2 can be forced, as shown by arrow 72, so that the first leg 6a inserts into the first mass 68 and that the second leg 6b inserts into the second mass 70. FIG. 42 illustrates that the attachment device 2 can be released from having the first configuration. The attachment device 2 can revert to having substantially the second configuration, causing the legs 6a and 6b to rotate inward, shown by arrows 78, applying force, shown by arrows 80, to the first mass 68 and the second mass 70 such that the first and second masses 68 and 70 move toward each other.

The attachment device 2 can be removed from the second mass 70 and/or the first mass 68, when applicable, by reversing the steps of the deployment methods supra.

Figure 43:
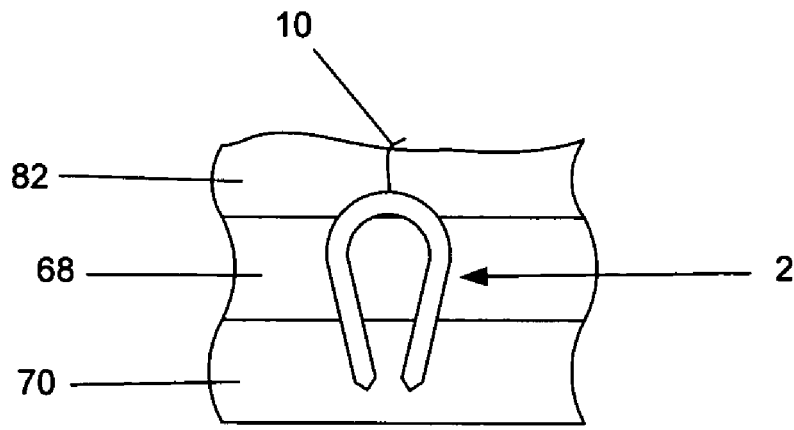
FIG. 43 is a cross-section illustrating a method of using the flag.

FIG. 43 illustrates that, during use, the attachment device 2 can be covered by new tissue growth 82. The flag 10 can extend outside of the new tissue growth 82 (as shown) or be located just below the surface but palpable. The flag 10 can act as a marker, palpable or visible by direct vision or imaging modalities known in the art (e.g., x-ray, magnetic resonance imaging (MRI), ultrasound, computed tomography (CT), echocardiogram) for example to locate the attachment device 2 in case of removal of the attachment device 2. The flag 10 can be made of, for example, suture material (e.g., Nylon, polyglycolic acid, polyester such as DACRON® from E.I. du Pont de Nemours and Company, Wilmington, Del., metals such as those used in the other elements of the attachment device 2, other polymers or combinations thereof). The base 4 can also serve this function (e.g., of a marker) in some applications.

Figure 44:
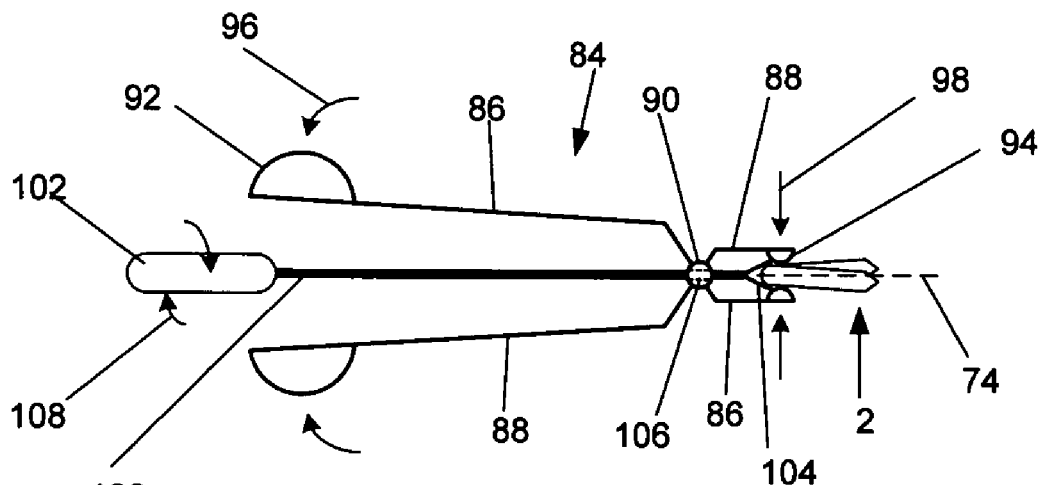
FIG. 44 illustrates an embodiment of the tool for deploying the attachment device.

FIG. 44 illustrates a tool 84 for deploying the attachment device 2. The tool 84 can have a first lever 86 and a second lever 88. The first lever 86 can be rotatably attached to the second lever 88 at a pivot 90. The first and second levers 86 and 88 can have a handle 92 at each lever's first end and a pad 94 at each lever's second end. The pads 94 can be used to hold the attachment device 2. When a force is applied to the handles 92, shown by arrows 96, the force is transmitted, shown by arrows 98, to the pads 94.

A driver shaft 100 can have a driver handle 102 at a first end and grips 104 at a second end. The pivot 90 can have a longitudinal channel 106. The driver shaft 100 can pass through the longitudinal channel 106 and/or be rotatably mounted to a case (not shown) fixed to a lever 86 or 88. The grips 104 can be releasably attached to the attachment device 2. The attachment device 2 can be rotated about the longitudinal axis 2 by releasing the pads 94 and rotating, as shown by arrows 108, the driver handle.

Figure 45:
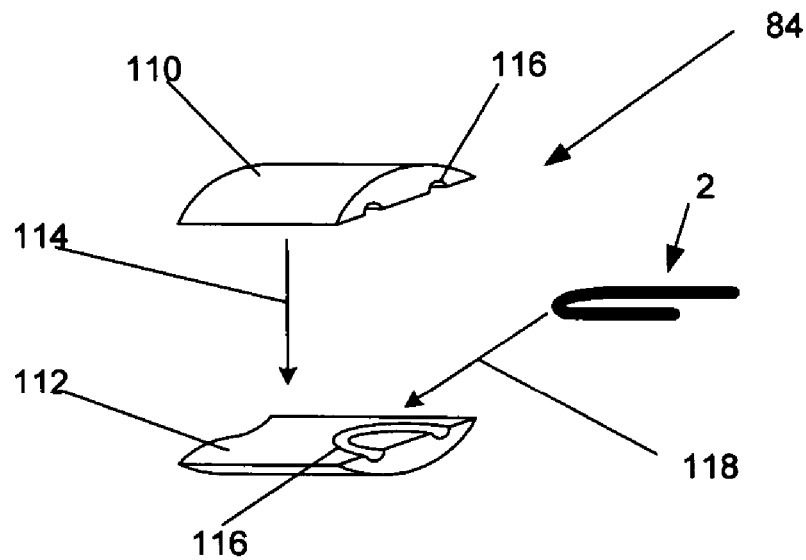
FIG. 45 illustrates the end of a tool for deploying the attachment device.

FIG. 45 shows the end of a tool 84 for deploying the attachment device 2 before the attachment device 2 has been loaded into the tool 84. The tool 84 can have a top part 110 and a bottom part 112. The top part 110 can be removably attached to the bottom part, as shown by arrow 114.

The top part 110 and/or the bottom part 112 can have grooves 116 sized to fit the base 4 and a portion of one or more legs 6 when the attachment device 2 has the first configuration. The attachment device 2 can be forced to have the first configuration and be loaded into the tool 84, as shown by arrow 118. The top part 110 can be attached to the bottom part 112 with the attachment device 2 seated (not shown) in the grooves 116.

The attachment device 2 can be placed at a desired deployment site by the tool 84. The device 2 can be deployed from the tool 84 by removing the top part 110 from the bottom part 112, and removing the tool 84 from the deployment site.

Figure 46:
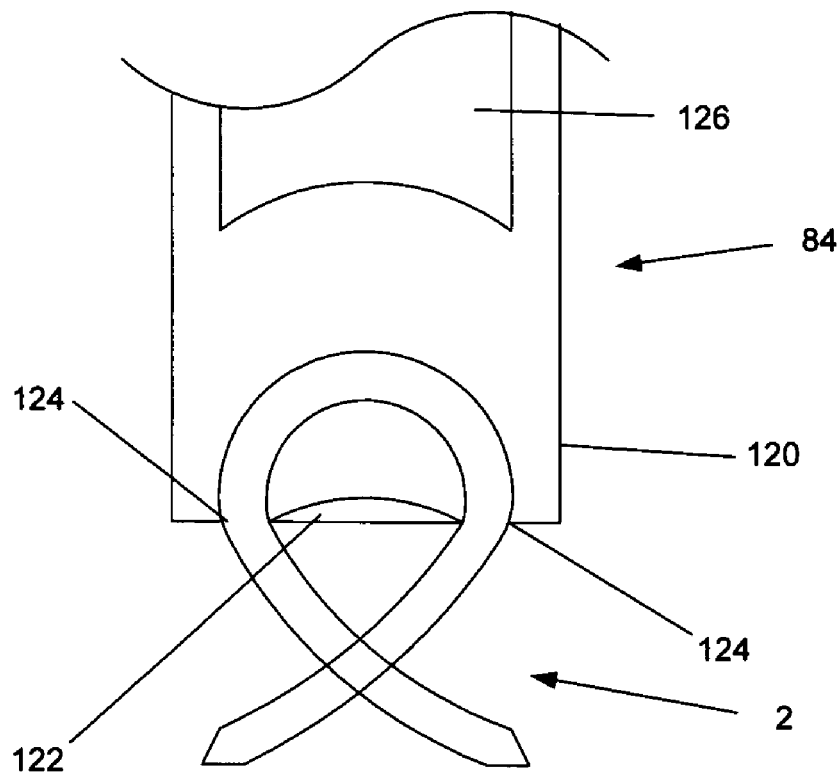
FIGS. 46 and 47 illustrate using the tip of an embodiment of the tool to deploy the attachment device.

FIG. 46 illustrates an end of a tool 84. The tool 84 can have a case 120 with an anvil 122 and leg ports 124. The case 120 can be slidably attached to a slide 126. The attachment device 2 can be loaded around the anvil 122. The legs 6 can protrude from the case 120 through the leg ports 124.

Figure 47:
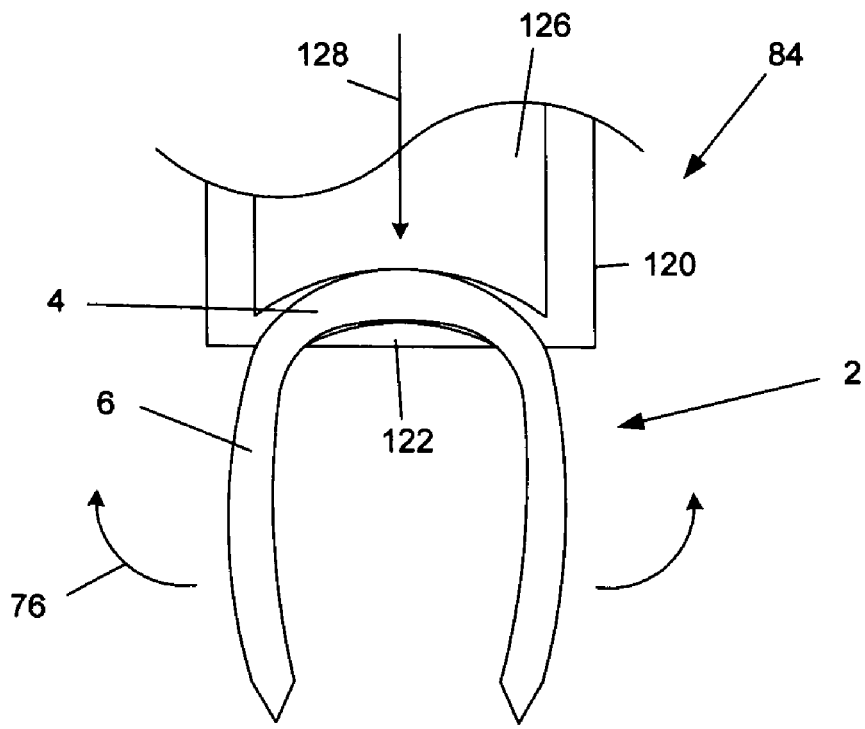

FIG. 47 illustrates a method of using the tool 84 of FIG. 46 to deploy the attachment device 2. The slide 126 can be forced, as shown by arrow 128, toward the anvil 122. The slide 126 can push the base 4 against the anvil 122, causing the legs 6 to rotate outward, as shown by arrows 76. The surface geometry of the anvil 122 and the slider 126 can match the surface geometry of the attachment device 2, when the attachment device is fully strained, as shown in FIG. 39. The attachment device 2 can then be inserted into the desired deployment site (not shown). When the attachment device 2 is in place, the attachment device 2 can be deployed from the tool 84, for example, by sliding the anvil 122 out of the way (perpendicular to the plane of FIG. 47) and forcing the attachment device 2 out the end of the tool 84 with the slide 126.

The ends of the tools 84 shown in FIGS. 45 through 47 can be pivoted to the remainder of the tool 84 by methods known to those having ordinary skill in the art. The pivotable end of the tool 84 can improve access to deployment sites not as easily accessible by a non-articulating tool 84. The tool 84 can be non-articulatable. It would also be possible when access to the site of implantation allows, to employ a tool substantially similar to a needle driver tool known to those skilled in the art.

Additional disclosure is included in U.S. patent application Ser. Nos. 10/327,821 and 10/646,639, filed 20 Dec. 2002 and 22 Aug. 2003, respectively, which are hereby incorporated by reference in their entireties. It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure.

We claim:

1. A method for attaching a heart valve prosthesis to a tissue annulus using an attachment device comprising a base and a pair of legs extending from the legs, the attachment device being elastically movable from a relaxed state wherein the legs cross one another and a delivery state wherein the legs extend substantially parallel with one another, the method comprising:
   loading the attachment device into a tool with the attachment device in the relaxed state;
   securing the heart valve prosthesis to the tissue annulus using the attachment device while applying a force using the tool to place the attachment device in the delivery state; and
   releasing the attachment device from the tool such that the attachment device returns towards the relaxed state such that the legs cross one another,
   wherein the heart valve prosthesis comprises a first prosthesis and a second prosthesis, and
   wherein securing the heart valve prosthesis to the tissue annulus comprises:
   securing the first prosthesis to a tissue annulus by inserting a plurality of attachment devices through the first prosthesis; and
   thereafter placing the second prosthesis, and
   wherein each attachment device is delivered by:
   a) holding the attachment device in the tool in the relaxed state;
   b) applying a force with the tool to force the attachment device to the delivery state;
   c) inserting the legs through the first prosthesis into tissue with the attachment device in the delivery state; and
   d) deploying the attachment device from the tool such that the attachment device returns towards the relaxed state.

2. The method of claim 1, wherein the legs cross one another at a leg angle less than one hundred eighty degrees (180°) in the relaxed state.

3. The method of claim 2, wherein the leg angle is less than or equal to ninety degrees (90°) in the relaxed state.

4. The method of claim 1, wherein the base rotates about a base axis when the attachment device is released, thereby causing the legs to cross one another.

5. The method of claim 1, wherein the force applied to place the attachment device in the delivery state comprises a base torque.

6. The method of claim 1, wherein the force applied to place the attachment device in the delivery state comprises a pivot torque.

7. The method of claim 1, wherein the attachment device is used to implant the heart valve prosthesis in a supra-annular position.

8. The method of claim 1, wherein the attachment device is used to implant the heart valve prosthesis in an infra-annular position.

9. The method of claim 1, wherein the first prosthesis comprises a sewing ring and the second prosthesis comprises a valve structure.

10. The method of claim 1, further comprising loading a pledget onto the attachment device before securing the heart valve prosthesis.

11. The method of claim 1, wherein the attachment devices are used to secure the first prosthesis in a supra-annular position.

12. The method of claim 1, wherein the attachment devices are placed within or around the tissue annulus to secure the first prosthesis to the tissue annulus.

13. The method of claim 1, wherein the attachment devices are placed vertically or horizontally within or around the tissue annulus to secure the first prosthesis to the tissue annulus.

14. The method of claim 1, wherein the first prosthesis comprises a sewing ring, and wherein the first prosthesis is attached prosthesis to a tissue annulus by inserting the attachment devices through the sewing ring.

15. The method of claim 1, wherein the tool comprises an anvil, and step a) comprises loading the attachment device around the anvil in the relaxed state.

16. The method of claim 1, wherein the tool comprises a slide and an anvil for causing the legs of the attachment device to rotate outward to the delivery state during step b).

17. The method of claim 16, wherein step d) comprises sliding the anvil out of the way and forcing the device out the end of the tool with the slide.

18. The method of claim 1, wherein the tool retains the attachment device in the delivery state while the device is inserted through the first prosthesis into tissue, whereupon the device is deployed from the tool.

19. The method of claim 1, wherein the legs of the attachment devices comprise tips with straight pointed ends.

20. The method of claim 1, wherein delivery of at least one of the attachment devices further comprises removing the attachment device from the sewing ring and tissue.

21. The method of claim 20, wherein delivery of the at least one of the attachment devices further comprises redeploying the attachment device at another location.

* * * * *